United States Patent [19]

Iimori

[11] Patent Number: 5,817,141
[45] Date of Patent: Oct. 6, 1998

[54] LOW FREQUENCY THERAPEUTIC DEVICE AND METHOD

[76] Inventor: Masataku Iimori, 15-21, Yakushimachi 1-chome, Yamagata-shi, Yamagata-ken, Japan

[21] Appl. No.: 698,884

[22] Filed: Aug. 16, 1996

[51] Int. Cl.$^6$ ........................................................ A61N 1/36
[52] U.S. Cl. .................................................. 607/76; 607/46
[58] Field of Search .................................. 607/46, 50, 63, 607/76, 148, 149, 153, 117; 128/897, 898

[56] References Cited

U.S. PATENT DOCUMENTS

| | | | |
|---|---|---|---|
| 4,102,347 | 7/1978 | Yukl ............................................. | 607/46 |
| 4,102,348 | 7/1978 | Hihara et al. ................................ | 607/63 |
| 4,738,250 | 4/1988 | Fulkerson et al. ........................... | 607/63 |
| 4,875,484 | 10/1989 | Anzai et al. ................................. | 607/46 |
| 5,131,389 | 7/1992 | Giordani ...................................... | 607/76 |
| 5,251,623 | 10/1993 | Groux et al. ................................ | 607/50 |
| 5,501,705 | 3/1996 | Fakhri ........................................ | 607/149 |

FOREIGN PATENT DOCUMENTS

| | | | |
|---|---|---|---|
| 0 290 126 | 11/1988 | European Pat. Off. .......... | A61N 1/32 |
| 0 293 068 | 11/1988 | European Pat. Off. .......... | A61N 1/32 |
| 2 351 671 | 12/1977 | France ............................... | A61N 1/32 |
| 2607708A | 6/1988 | France ..................................... | 607/148 |
| 2 673 378 | 9/1992 | France ............................... | A61N 1/18 |

*Primary Examiner*—William E. Kamm
*Assistant Examiner*—Carl H. Layno
*Attorney, Agent, or Firm*—Helfgott & Karas, P C.

[57] ABSTRACT

A therapeutic device including a voltage adjustment for outputting an adjusted AC signal to a load. The adjusted AC signal has an amplitude between 0 and 100 volts and a low commercial frequency. To create and output this signal, the device accepts an input voltage from a commercially available power supply and uses a pair of contact electrodes attached to two arbitrarily selected points on the load. The device has an electrical current setting circuit which assigns a prescribed current set value between the selected points. The actual therapeutic electric current applied between these points is a function of the setting of the voltage adjustment and of the load resistance between these points. A comparing circuit in the therapeutic device compares the therapeutic electric current flowing between the two points with the prescribed current set value. If the therapeutic electric current is larger than the prescribed current set value, then the comparing circuit causes an output switch to interrupt the supply of the adjusted voltage to the pair of contact electrodes. In the specified embodiments of this device, the load between the contact electrodes includes a series connection between a therapist and a patient.

10 Claims, 4 Drawing Sheets

LOW FREQUENCY THERAPEUTIC DEVICE AND METHOD

FIELD OF THE INVENTION

This invention relates to a low frequency therapeutic device used for weak electric current therapy wherein alternating current is introduced to human body and a therapeutic method for human body which is performed by the use of this low frequency therapeutic device and which can be carried out non-invasively by a non-medical person.

BACKGROUND OF THE INVENTION

In conventional low frequency therapeutic devices, known is a device from which an alternating current having a frequency of 100 Hz to several kHz is output to be introduced to a patient through electrodes. For instance, Japanese Patent Laid-open No. 195565/1983 discloses a therapeutic device which outputs two types of alternating current of around 11 kHz and around 250 Hz, respectively, wherein it is intended to invigorate muscles by means of the alternating current of 11 kHz being a medium frequency, and at the same time analgesic action is given by the alternating current of 250 Hz being a low frequency.

Up to now, it has been considered in conventional low frequency therapeutic devices which output an alternating current that invigorating effects of muscles and analgesic action appear in a frequency range of 100 Hz to several kHz.

On one hand, it is theoretically believed that the higher electric current value to be introduced to a patient from a low frequency therapeutic device results in the higher therapeutic effects per unit time. From a legal point of view, however, the upper limit of an output electric current is specified as 20 mA according to the standard for approving the production of medical devices (Japanese Ministry of Health and Welfare).

However, in conventional low frequency therapeutic devices which output alternating current, when the electric current value to be introduced to a patient is increased, the stimulation becomes too strong for the patient, resulting in an interference of therapeutic effects. This is because an alternating current having a substantially rectangular waveform is output in a frequency of several kHz. This phenomenon is the same as that also in a frequency range in the vicinity of 100 Hz, and there is still such a tendency that the stimulation given to a patient are too strong, because a leading edge of the electric current waveform is still steep in this frequency range.

Because of the reasons as described above, an electric current value cannot be so increased in order to suppress the stimulation due to a leading edge of electric current, so that in reality, an electric current value does not exceed about several mA. Therefore, efficient therapeutic effects could not have been attained by the conventional low frequency therapeutic devices.

On the other hand, in a conventional low frequency therapeutic method, it has been practiced in such that electrodes connected to the output terminals of the low frequency therapeutic device come into directly contact with proper sites ("TSUBO" in Japanese, and it means a therapeutic point) on the body of a patient, these electrodes are secured by means of an adhesive tape or the like, and then an electric current is passed through these electrodes. In the method as described above, however, there is such a problem that when TSUBO (or therapeutic points) exist on an irregular part (for example, that extends around the neck) on the surface of a patient's body, electrodes to be attached are difficult to secure on the patient's body. Moreover, when a therapist intends to move the electrodes to other therapeutic points on the patient's body during the therapy, the adhesive tape once applied must be removed and again applied on all such occasions, so that it is troublesome and a period of time required for the therapy is prolonged.

SUMMARY OF THE INVENTION

An object of the present invention is to provide a low frequency therapeutic device which can increase substantially therapeutic effects per unit time while suppressing the stimulation given to a patient.

Another object of the present invention is to provide a therapeutic method by which a transfer of electrodes being in contact with respective sites on the patient's body can easily and instantly be carried out.

According to the present invention, there is provided a low frequency therapeutic device comprising a voltage adjusting means for outputting an adjusted voltage of a commercial frequency which has been adjusted to 0 to 100 volts by inputting a voltage having the commercial frequency from a commercially available power supply; a pair of contact electrodes being in contact with two arbitrary points on a load and flowing a therapeutic electric current between these two points in response to the adjusted voltage inputted from the voltage adjusting means and a load resistance existing between the two points; an electric current setting means for setting an electric current to be flowed between the two points to a prescribed set value; a comparing means for comparing the therapeutic electric current flowing between the two points with an electric current of the prescribed set value; and a control means for interrupting a supply of the adjusted voltage to the pair of contact electrodes in the case when it is detected that the therapeutic electric current is larger than the prescribed set value as a result of inputting the comparative results from the comparing means.

Furthermore, according to the present invention, there is provided a therapeutic method comprising a step of outputting an adjusted voltage having a commercial frequency through a therapist and a patient from a low frequency therapeutic device in a situation where a first contact electrode being electrically connected to one of output terminals in the low frequency therapeutic device outputting said adjusted voltage of the commercial frequency which has been adjusted to 0 to 100 volts by inputting a voltage having the commercial frequency from a commercially available power supply comes into contact with a prescribed site on the surface of the therapist's body; another site on the surface of the therapist's body comes into contact with a first site on the surface of the patient's body; and a second contact electrode being electrically connected to the other output terminal in said low frequency therapeutic device comes into contact with a second site on the surface of the patient's body.

The present inventor has found that a leading edge of electric current is comparatively moderate in alternating current in the vicinity of a commercial frequency (50 or 60 Hz), and that in a frequency range lower than that of the commercial frequency (referred to as "ultra-low frequency range"), the stimulation which might be applied to a patient may be reduced to such a degree that they are substantially insensible by the patient. Thus, therapeutic effects can be remarkably enhanced by increasing an current while suppressing the stimulation given to a patient in this lower range than that of the commercial frequency.

Such an ultra-low frequency range can suitably be selected by a heretofore well-known frequency converter. It is, however, preferred that the ultra-low frequency range is kept at at least 1 Hz to maintain therapeutic effects.

Furthermore, in the therapeutic method according to the present invention, since a therapeutic electric current is introduced to a patient through a part of the body, for example, a hand of a therapist, a therapeutic site on the patient's body can instantly be changed by a hand of the therapist. Moreover, the therapist's hand can come into positively contact with an irregular part on the surface of the patient's body, whereby positive energization can be effected through the therapist's hand. Besides, when an area as to a therapeutic site of the patient being in contact with the therapist's hand is varied by means of the hand, the amount of stimulation given to the patient can also be adjusted.

On the other hand, it may be modified in the therapeutic method according to the present invention in such that one or more low frequency therapeutic devices are added, each pair of electrodes connected to the added low frequency therapeutic devices come into contact with other sites on the surface of the patient's body, and a therapeutic electric current is introduced to the patient's body through these electrodes together with the above-mentioned original energization path through the therapist's body. By this modification, therapeutic effects per unit time are more enhanced, and a period of time required for therapy is reduced.

DESCRIPTION OF THE PREFERRED EMBODIMENTS

A low frequency therapeutic device in the preferred embodiment according to the present invention will be described below.

Figure 1:
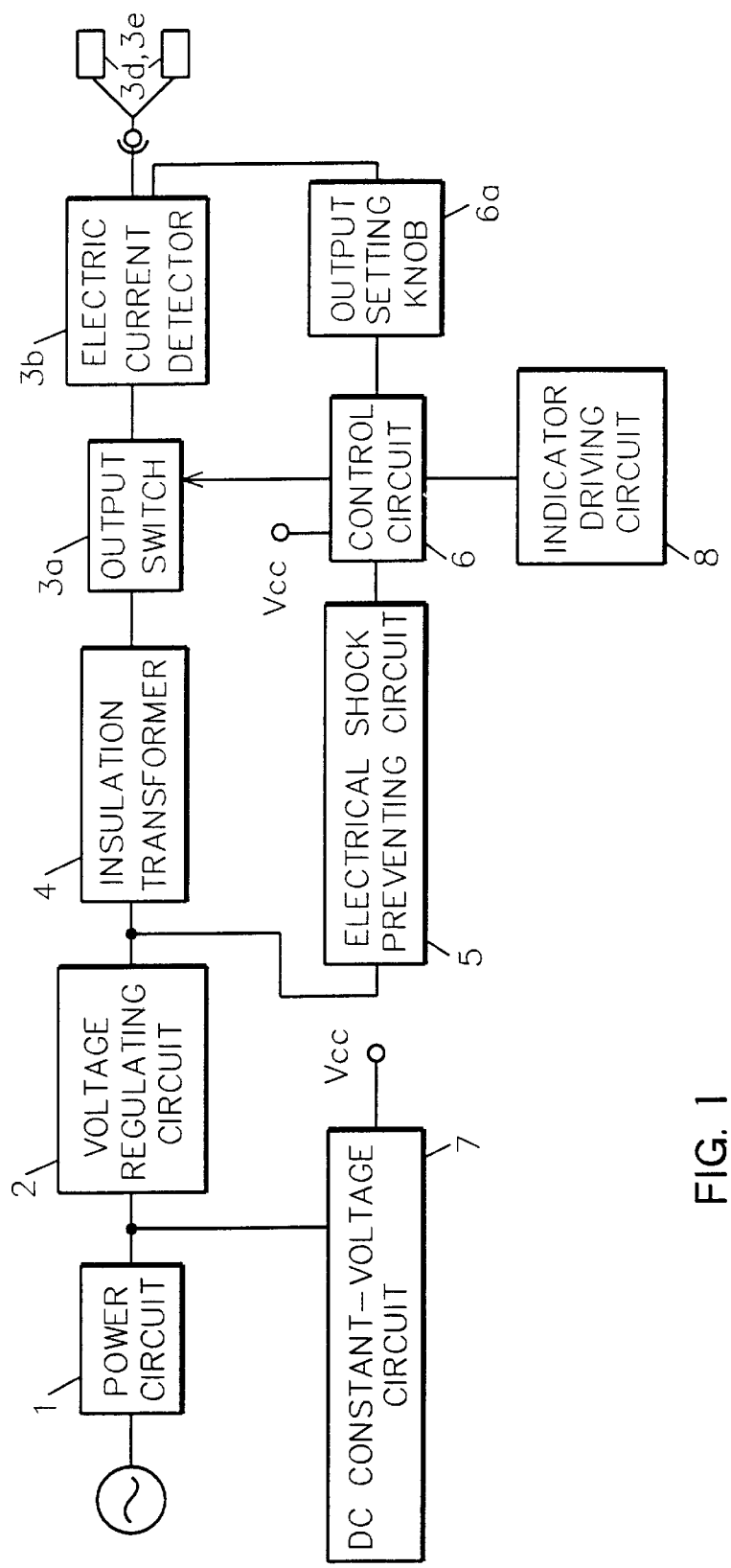
FIG. 1 is a block diagram showing a preferred embodiment of the circuit construction of a low frequency therapeutic device according to the present invention.
Figure 2:
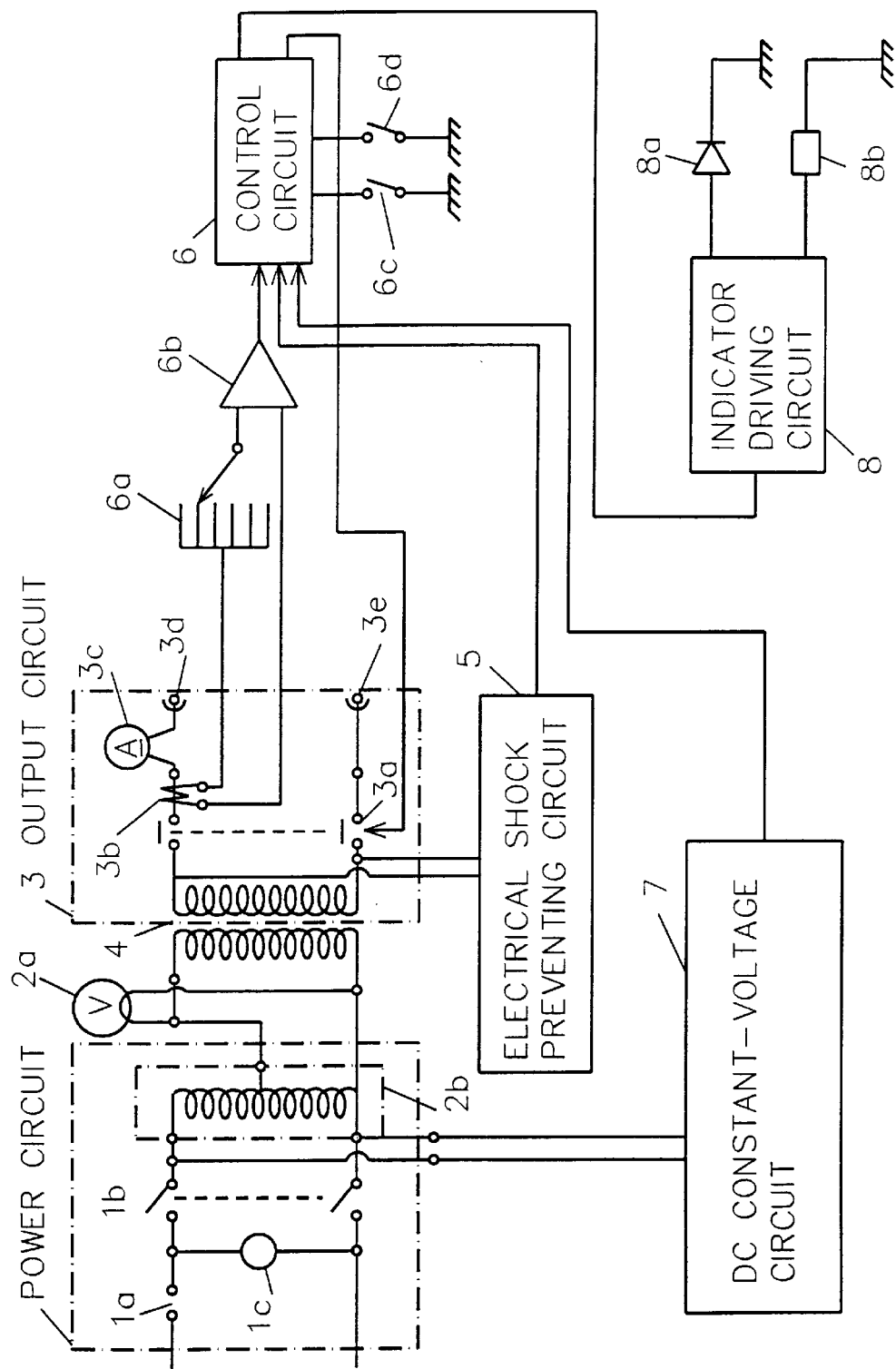
FIG. 2 is a partly block and a partly circuit diagram showing a more detailed circuit structure of the embodiment of FIG. 1.

FIGS. 1 and 2 show a circuit structure of the low frequency therapeutic device according to the present invention which is composed of a power circuit 1 including a power fuse 1a, a power switch 1b, and a power indicator lamp 1c; a voltage regulating circuit 2 including an indicating voltmeter 2a, and an output adjustment knob (variable autotransformer) 2b for adjusting output voltage; an output circuit 3 including an output switch 3a, an electric current detector 3b, an indicating ammeter 3c, and therapeutic electrodes 3d, 3e; a 1:1 insulation transformer 4 for insulating the power circuit 1 from the output circuit 3; an electrical shock preventing circuit 5; a control circuit 6 including an output setting knob 6a, a comparator 6h, an operation button switch 6c, and a reset button switch 6d; a DC constant-voltage circuit 7 for supplying operating current of the control circuit 6; and an indicator driving circuit 8 including a running indicator 8a and a buzzer 8b.

In the above described circuit, an output of 100 volt AC voltage supplied by turning ON the power switch 1b of the power circuit 1 is adjusted (0 to 100 volts) by the output adjustment knob 2b, so that an electric current in response to a resistance value caused by connecting the therapeutic electrodes 3d and 3e to a body of either a patient or a therapist (not shown, but see FIG. 3 as to a connection example) flows.

In this connection, an upper limit of the electric current to be output may be set in six levels of current values, i.e., 4, 6, 7, 8, 9, and 10 m, respectively, by means of the output setting knob 6a. Accordingly, when the output setting knob 6a is set at a desired position, a reference voltage (which is determined by a value selected by the output setting knob 6a) obtained from the DC constant-voltage circuit 7 is compared with a voltage obtained by converting a current flowing through the output circuit 3 in response to the applied voltage which has been adjusted by the output adjustment knob 2b in the comparator 6b contained in the control circuit 6. When an electric current exceeding the reference voltage flows through the output circuit 3, the output switch 4 turns OFF.

For such a possible occasion where the passage of electric current on the output side is interrupted due to power outage and the like, or an overcurrent flows through the output circuit 3 due to any reason so that the output switch 3a has turned OFF, the therapeutic device is arranged so as not to be reenergized until the electric charge which has been held in the electrical shock preventing circuit 5 disappears as a result of returning the output adjustment knob 2b to the zero position, and further an operator must push the operation button switch 6c to restart the device.

While the running indicator 8a is lit up during energization to the output side, when the output switch 4 is in an OFF state, the running indicator 8a flashes and issues an alarm by sounding the buzzer 8b. This flashing of the running indicator 8a and the sounding of the buzzer 8b are released by pushing the reset button switch 6d.

In the present embodiment, while the circuit has been composed so as to output the same frequency as that of commercial frequency, when it is desired to obtain an output current having less frequency than that of commercial frequency, it may be adapted that a frequency converter well known in the art is disposed in the power circuit 1 or the like to output an input frequency after converting the same.

Next the preferred embodiments of the therapeutic method according to the present invention will be described.

There are two ways of a therapy wherein the low frequency therapeutic device according to the present invention is employed. Namely, one of the ways of the therapy is such that output terminals extending from the low frequency therapeutic device are attached to prescribed sites of a patient body, and an electric current is directly introduced to the patient. The other of the therapeutic ways is the one wherein one end of an output terminal is attached to a body (e.g., a hand) of a person who carries out a therapy (hereinafter referred to as "therapist"), while the other end of the output terminal is attached to a body of a patient, and when the other hand of the therapist comes into contact with the patient body, an electric current is introduced to the patient through the therapist's body. Though therapeutic effects can be obtained, of course, by the former way, the latter way is more preferable because an amount of energization and a site to be energized (a so-called "TSUBO" in Japanese) can be delicately controlled by adjusting a degree of contact with the patient body by means of the therapist's hand.

Figure 3:
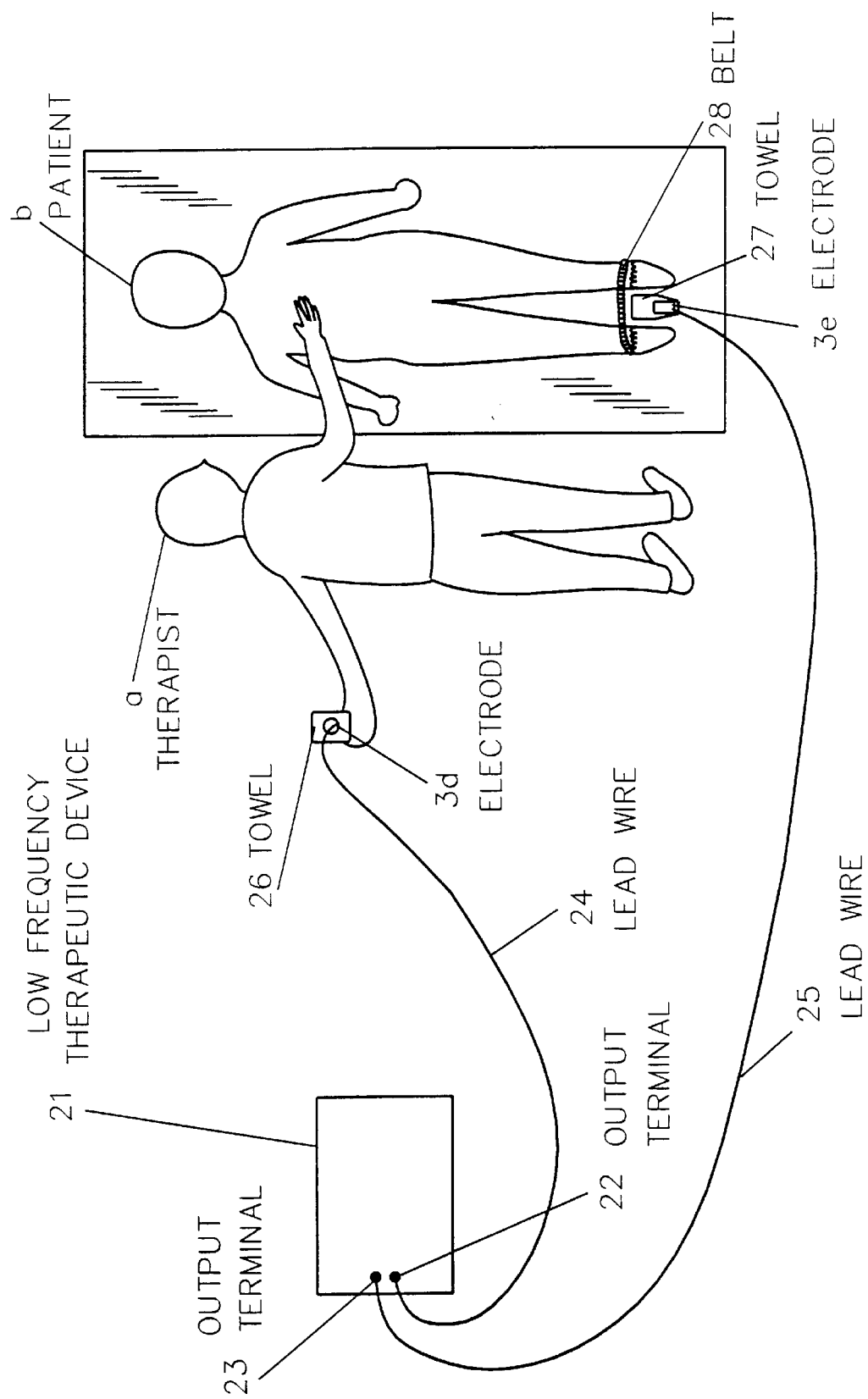
FIG. 3 is a schematic view showing a first preferred embodiment of the therapeutic method according to the present invention.

FIG. 3 shows conceptually the first embodiment of the therapeutic method according to the present invention wherein the above described latter way has been adopted.

A lead wire 24 connected to an output terminal 22 of a low frequency therapeutic device 21, which is the same as the low frequency therapeutic device 21 explained above, is linked to a therapeutic electrode 3d which is wrapped up in a towel containing a suitable amount of moisture and grasped by one hand of a therapist a. In this case, the therapist a may tread on the towel wrapping up the therapeutic electrode 3d by the sole of his (or her) foot to come in contact therewith thereby attaining energization.

On the other hand, a lead wire 25 linked to an output terminal 23 of the low frequency therapeutic device 21 is connected to a therapeutic electrode 3e which is wrapped up in a towel 27 containing a suitable amount of moisture and sandwiched between the ankles of patient's both legs. A belt 28 is wound around both the ankles in a state where the towel is sandwiched between the ankles of the patient b in such that the towel 27 is in contact with the ankles at a constant force.

In this situation, the therapist a turns ON a power switch of the low frequency therapeutic device 21, and the other free hand of the therapist a contacts with a prescribed site (therapeutic point) of the patient b while controlling the voltage and the current to predetermined values, respectively, whereby a low frequency electric current is energized with respect to the patient b.

According to the method as described above, an amount of energization and a site to be energized can be finely adjusted by the side of the therapist a. Furthermore, since the energization is effected on the body of the patient b through the therapist a, the stimulation to be given to the patient b is much more moderated. In a fine adjustment of an amount of energization, when the therapist a grips firmly the towel 26, an amount of energization increases comparatively, while the towel 26 is lightly grasped by the therapist a, an amount of energization decreases relatively. In the manner wherein the towel 26 is trod by the foot of the therapist a as described above, an amount of energization can be adjusted by moderating the force for treading the towel 26 by the therapist a.

On one hand, concerning a fine adjustment of a site to be energized, such energizing site can freely be changed by varying an area wherein a hand of the therapist a comes in contact with the patient b. In addition, since changes in a site to be energized is performed by a hand of the therapist a, there is no need for working in rearrangements of the therapeutic electrodes 3d and 3e as occasion demands, so that such changes can be carried out extremely rapidly. As a result, a time required for a therapy is reduced so that an efficient therapy can be attained. Furthermore, human body has not a flat profile, but there is partly irregular, and there is a site to be energized having a narrow area (for example, peripheries of a nape, armpits, peripheries of a finger and the like), so that it may be said that use of a hand of the therapist a is optimum in order to be in suitably contact with such target site as described above to achieve desired energization.

Figure 4:
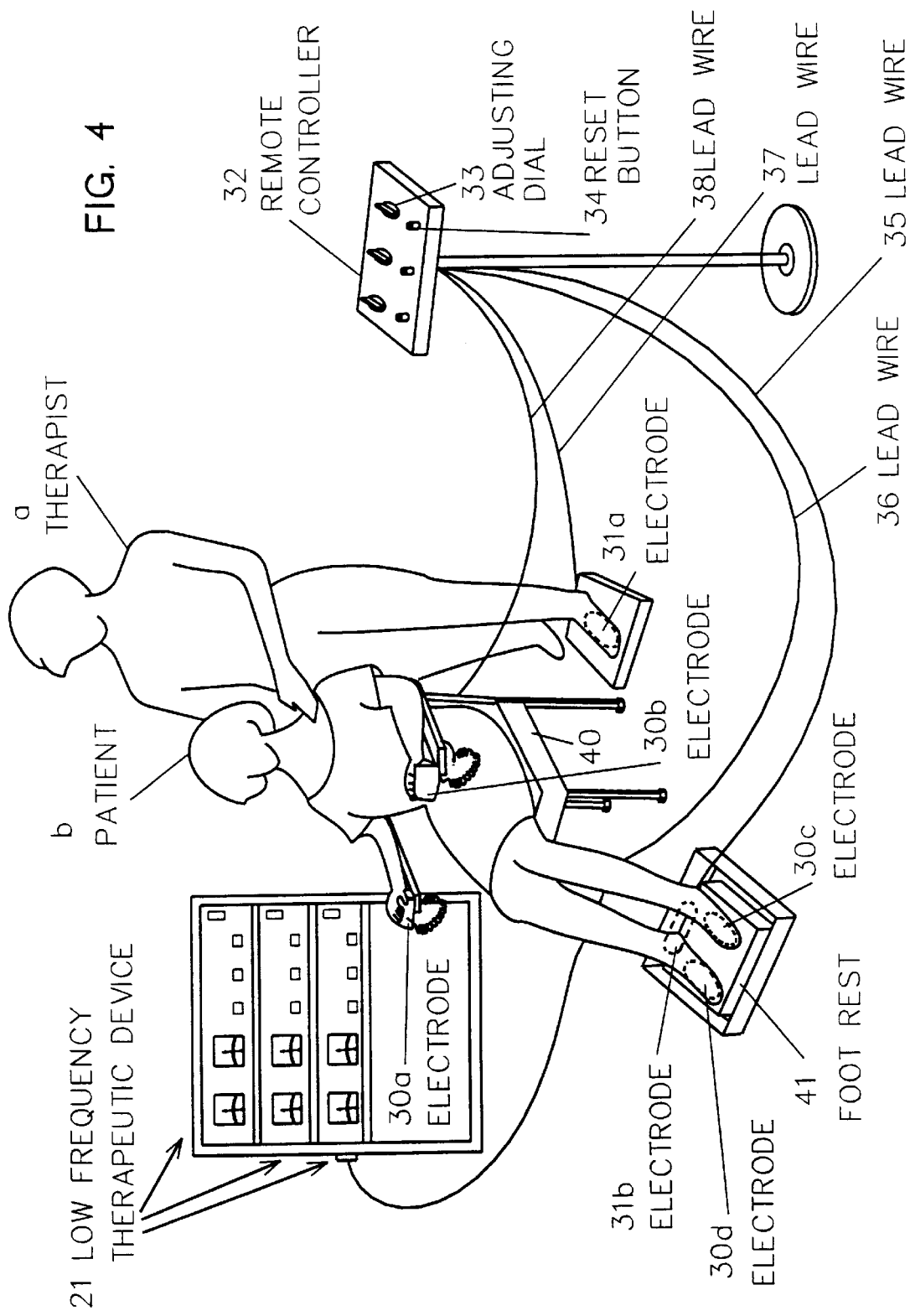
FIG. 4 is a perspective view showing a second preferred embodiment of the therapeutic method according to the present invention.

FIG. 4 shows conceptually a second embodiment of the therapeutic method according to the present invention.

In the second embodiment, three energization loops are prepared, and more specifically there are two of second and third energization loops in each of which an electric current passes from a patient's hand to the patient's foot in addition to a first energization loop wherein an electric current passes from a site with which a therapist's hand is in contact to a foot of the patient. For this purpose, three low frequency therapeutic devices 21 are prepared with respect to each energization loop, where the three low frequency therapeutic devices 21 are the same as the low frequency therapeutic device 21 used in the first embodiment.

As shown in FIG. 4, the first energization loop is formed in a path wherein an output terminal of the first low frequency therapeutic device 21 is connected to a pedal electrode 31a through one line of lead wires 36 (composed of two cores per each of three low frequency therapeutic devices, i.e., there are the total six cores), a remote controller 32, and a lead wire 37 (disposed in such that it is trod by the a foot of a therapist a), the first energization loop reaches a therapeutic site of a patient b (the patient's neck in case of FIG. 4) through the interior of the therapist's body (from a foot to a hand), it further reaches a therapeutic electrode 31b being in contact with right and left heels of the patient b through the interior of the patient's body, and from the therapeutic electrode 31b it returns to the other output terminal of the low frequency therapeutic device 21 through one line of lead wire (three cores) 35, the remote controller 32, and one line of the lead wire 36.

The second and the third energization loops are formed in pathes in each of which an output terminal of the second low frequency therapeutic device (or the third low frequency therapeutic device) 21 reaches a therapeutic electrode 30a (or a therapeutic electrode 30b) being in contact with a right palm (or a left palm) of the patient b through the lead wire 36, the remote controller 32, and one line of a lead wire 38 (two cores), the second energization loop (or the third energization loop) reaches further a therapeutic electrode 30c (or a therapeutic electrode 30d) being in contact with the back of a right tiptoe (or a left tiptoe) of the patient b through the interior of the patient's body, and from the therapeutic electrode 30c (or the therapeutic electrode 30d) it returns to the other output terminal of the second low frequency therapeutic device (or the third low frequency therapeutic device) 21 through one line of the lead wire (three cores) 35, the remote controller 32, and one line of the lead wire 36, respectively.

As described above, the first to the third energization loops are three electric current pathes which are independently provided. It is, however, to be noted that an electric current path through the interior of a human body depends upon "KEIRAKU" in Japanese (it means arteries and veins) of human body (it is considered in the field of electrical therapy that an electric current flows usually along "KEIRAKU" existing between two electrodes having different polarities from one another). For this reason, if the "KEIRAKU" is partially branched, there is a possibility such that electric currents intersect with each other at a certain point existing among the first to the third energization loops. In other words, it may be considered that each of three energization loops is not perfectly independent. For instance, it may be interpreted with respect to a relationship between the second and the third energization loops that an electric current flows from the therapeutic electrode 30a as to the right hand of the patient b to the therapeutic electrodes 30c, 30d, and 31b as to the patient's right foot, left foot, and heels, respectively, or another electric current flows from the therapeutic electrode 30b with respect to the left hand of the patient b to the therapeutic electrodes 30c, 30d, and 31b relevant to the patient's right foot, left foot, and heels, respectively.

In the present embodiment, a further electric current path may be increased in addition to the second and the third energization loops. On the contrary, either only the second or the third energization loop may be employed. It is however, to be noted that a therapeutic effect per unit time increases usually in proportion to the number of energization loops.

In the present embodiment, as shown in FIG. 4, armrests of a chair 40 are provided with the therapeutic electrodes 30a and 30b as to the patient's right and left hands, respectively, so that the patient b can receive a treatment by the therapist a while maintaining his (or her) comfortable posture. In this case, the chair 40 may also be a reclining type. The therapeutic electrodes 30c, 30d, and 31b with reference to the patient right foot, left foot, and heels are mounted on a suitable foot rest 41.

The therapeutic electrodes 30a through 30d and 31b as well as the pedal electrode 31a are disposed in a state where each of these electrodes is wrapped up in a towel containing a suitable amount of water as in the case of the first embodiment. In this case, the towel may be replaced by other materials so far as they can contain a suitable amount of moisture therein such as nonwoven fabrics and the like. Furthermore, a fastening belt (not shown) may be provided for maintaining a constant contacting state defined between the feet of the patient b and the therapeutic electrode 30b, 30d, or 31b, respectively.

The remote controller 32 is provided with adjusting dials 33 for adjusting a voltage to be applied to the respective first to third energization loops (which has the same functions as that of the aforementioned output adjustment knob 2b) and reset buttons 34 (having the same functions as that of the above-mentioned reset button switch 6d) in every energization loops. The remote controller 32 makes the operation for adjusting a voltage, or the like operation by the therapist a easy in the case where the low frequency therapeutic devices 21 are placed apart from the patient b.

Operation for the low frequency therapeutic devices 21 in the present embodiment is carried out in accordance with the same manner as that of the first embodiment as follows. Namely, the therapeutic electrodes 30a through 30d and 31d come into contact with respective sites (feet are in a barefooted state) in the body of the patient b, and the therapist a turns ON the power switches of the low frequency therapeutic devices 21 in a situation where the therapist a treads the pedal electrode 31a. When a hand of the therapist a comes in contact with a prescribed site (therapeutic point) in the body of the patient b while controlling the voltage and the electric current to a predetermined values, respectively, a low frequency electric current is supplied to the patient b. In this case, it is preferred to arrange the second and third energization loops in such that a comparatively low electric current (e.g., 3 mA current) flows through each of the loops, because a hand is usually sensitive to electric current.

According to the present embodiment, an increase in an amount of energization per unit time is attained by means of a plurality of the first to the third energization loops while suppressing an increase in electrical the stimulation with respect to the patient b, so that electrical therapeutic effects are obtained for a short period of time. Besides, mutual effects among the first to the third energization loops by which the "KEIRAKU" in the whole body are efficiently stimulated at the same time, whereby more uniform therapeutic effects can be expected are obtained.

Although the invention has been described with respect to specific embodiments for complete and clear disclosure, the appended claims are not to be thus limited, but are to be construed as embodying all modifications and alternative constructions that may be occurred to one skilled in the art which fairly fall within the basic teaching here is set forth.

What is claimed is:

1. A low frequency therapeutic device comprising:
    a voltage adjusting means for outputting an adjusted voltage with an unaltered commercial frequency, said voltage adjusting means inputting a voltage with said commercial frequency from a commercially available low frequency alternating-current power supply and adjusting said voltage to 0 to 100 volts;
    a pair of contact electrodes coupled to said voltage adjusting means and being in contact with two arbitrary points on a load, said electrodes flowing a therapeutic electric current between said two points in response to said adjusted voltage from said voltage adjusting means and a load resistance existing between said two points;
    an electric current setting means for setting an electric current to be flowed between said two points to a prescribed set value;
    a comparing means for comparing the therapeutic electric current flowing between said two points with an electric current of said prescribed set value; and
    a control means for interrupting a supply of said adjusted voltage to said pair of contact electrodes in the case when it is detected that said therapeutic electric current is larger than said prescribed set value as a result of inputting the comparative results from said comparing means.

2. A low frequency therapeutic device as claimed in claim 1 wherein said control means comprises an output switch.

3. A therapeutic method comprising: placing a first contact electrode of the output terminal of a low frequency therapeutic device on the surface of a therapist's body at a prescribed site;
    moving another site on the surface of the therapist's body into contact with a first site on the surface of a patient's body;
    placing a second contact electrode of the output terminal of said low frequency therapeutic device on the surface of the patient's body at a second site; and
    flowing a therapeutic current through the therapist and the patient from said low frequency therapeutic device.

4. A therapeutic method as claimed in claim 3 further causing said therapeutic electric current flows between said prescribed site of the therapist and said second site of the patient in response to said adjusted voltage with said commercial frequency and a resistance existing between these sites.

5. A therapeutic method as claimed in claim 3, including converting a frequency of said therapeutic electric current is converted into a frequency lower than said commercial frequency.

6. A therapeutic method as claimed in claim 3 wherein said step of placing a first contact electrode includes placing said first contact electrode on either a hand or foot of the therapist, while another site of the therapist is the other hand thereof.

7. A therapeutic method as claimed in claim 3 wherein said step of placing a second contact electrode includes placing said second contact electrode the patient's feet.

8. A therapeutic method as claimed in claim 3 further comprising the step of wrapping said first and second contact electrodes in woven or non-woven fabric containing moisture.

9. A therapeutic method as claimed in claim 3 further providing at least one other low frequency therapeutic device being the same type as said low frequency therapeutic device, a third contact electrode extending from one of output terminals in said other low frequency therapeutic device comes into contact with a third site on the surface of the patient's body, a fourth contact electrode connected electrically to the other output terminal in said second low frequency therapeutic device comes into contact with a fourth site on the surface of said patient's body, and while maintaining this situation;

said adjusted voltage of the commercial frequency is output from said second low frequency therapeutic device through said patient at the same time of outputting the adjusted voltage from said Low frequency therapeutic device.

10. A therapeutic method as claimed in claim 9 wherein said other low frequency therapeutic devices and further providing are two of the second and the third low frequency therapeutic devices, a fifth contact electrode extending from one of output terminals in the third low frequency therapeutic device comes into contact with a fifth site on the surface of the patient's body, and a sixth contact electrode connected electrically to the other output terminal in said third low frequency therapeutic device comes into contact with a sixth site on the surface of said patient's body.

\* \* \* \* \*